(12) United States Patent
Fan et al.

(10) Patent No.: US 6,774,135 B2
(45) Date of Patent: *Aug. 10, 2004

(54) METHOD OF ENHANCING LYSOSOMAL α-GALACTOSIDASE A

(75) Inventors: Jian-Qiang Fan, Chiba (JP); Satoshi Ishii, Oita (JP)

(73) Assignee: Mount Sinai School of Medicine of New York University, New York, NY (US)

( * ) Notice: Subject to any disclaimer, the term of this patent is extended or adjusted under 35 U.S.C. 154(b) by 177 days.

This patent is subject to a terminal disclaimer.

(21) Appl. No.: 09/927,285

(22) Filed: Aug. 10, 2001

(65) Prior Publication Data

US 2002/0156100 A1 Oct. 24, 2002

Related U.S. Application Data

(63) Continuation of application No. 09/087,804, filed on Jun. 1, 1988, now Pat. No. 6,274,597.

(51) Int. Cl.[7] ................... A61K 31/445; A61K 31/435; C07D 211/40; C12N 9/40
(52) U.S. Cl. ................... 514/315; 514/317; 514/277; 514/281; 546/219; 435/208
(58) Field of Search ................ 514/315, 317, 514/277, 281; 546/219; 435/208

(56) References Cited

U.S. PATENT DOCUMENTS

| | | | |
|---|---|---|---|
| 4,639,436 A | 1/1987 | Junge et al. | 514/24 |
| 5,030,628 A | 7/1991 | Joyeau et al. | 514/315 |
| 5,043,273 A | 8/1991 | Scudder et al. | 435/131 |
| 5,051,407 A | 9/1991 | Boshegen et al. | 514/24 |
| 5,192,772 A | 3/1993 | Yoshikuni et al. | 514/315 |
| 5,250,545 A | 10/1993 | Tsuroka et al. | 514/328 |
| 5,292,750 A | 3/1994 | Yoshikuni et al. | 514/315 |
| 5,399,567 A | 3/1995 | Platt et al. | 514/315 |
| 5,504,078 A | 4/1996 | Ducep et al. | 514/43 |
| 5,561,221 A | 10/1996 | Yoshida et al. | 520/350 |
| 5,580,884 A | 12/1996 | Platt et al. | 514/315 |
| 5,596,005 A | 1/1997 | Wong et al. | 514/335 |
| 5,622,972 A | 4/1997 | Bryant et al. | 514/315 |
| 5,643,888 A | 7/1997 | Rohrschneider | 514/43 |
| 5,656,641 A | 8/1997 | Platt et al. | 514/315 |

(List continued on next page.)

FOREIGN PATENT DOCUMENTS

| | | | |
|---|---|---|---|
| JP | 61-280472 | 12/1986 | ........... C07H/15/18 |
| WO | WO87/03903 | 7/1987 | |
| WO | WO92/00277 | 4/1993 | |
| WO | WO95/19172 | 7/1995 | ......... A61K/31/445 |
| WO | WO99/24401 | 5/1999 | ......... C07D/211/46 |
| WO | WO00/29556 | 5/2000 | ........... C12N/5/12 |
| WO | WO 00/33843 | 6/2000 | |
| WO | WO00/56334 | 9/2000 | ......... A61K/31/445 |
| WO | WO00/62799 | 10/2000 | ......... A61K/31/445 |
| WO | WO01/07078 | 2/2001 | .......... A61K/38/47 |
| WO | WO01/10429 | 2/2001 | .......... A61K/31/00 |
| WO | WO94/26714 | 9/2001 | |

OTHER PUBLICATIONS

Pobojewski et al., "Experimental drug reverses effects of Fabry disease", The University Record (Univ. of Michigan), vol. 55, No. 34, p. 11, Jun. 2000.

(List continued on next page.)

Primary Examiner—Samuel Barts
Assistant Examiner—Michael C. Henry
(74) Attorney, Agent, or Firm—Darby & Darby

(57) ABSTRACT

A method of enhancing the activity of lysosomal α-Galactosidase A (α-Gal A) in mammalian cells and for treatment of Fabry disease by administration of 1-deoxy-galactonojirimycin and related compounds.

39 Claims, 13 Drawing Sheets

U.S. PATENT DOCUMENTS

| | | | |
|---|---|---|---|
| 5,691,306 A | 11/1997 | Bergeron et al. | 514/435 |
| 5,786,368 A | 7/1998 | Platt et al. | 514/315 |
| 5,798,366 A | 8/1998 | Platt et al. | 514/315 |
| 5,801,185 A | 9/1998 | Platt et al. | 514/315 |
| 5,844,102 A | 12/1998 | Sierks et al. | 536/17.2 |
| 5,863,903 A | 1/1999 | Lundgren et al. | 514/43 |
| 5,981,494 A | 11/1999 | Rademacher et al. | 514/23 |
| 6,177,447 B1 | 1/2001 | Aerts et al. | 514/319 |
| 6,225,325 B1 | 5/2001 | Jacob | 514/328 |
| 6,274,597 B1 * | 8/2001 | Fan et al. | |
| 6,291,657 B1 | 9/2001 | Platt et al. | 536/17.2 |
| 6,465,488 B1 | 10/2002 | Butters et al. | 514/315 |
| 2001/0018090 A1 | 8/2001 | Noda et al. | 426/597 |
| 2001/0044453 A1 | 11/2001 | Jacob et al. | 514/328 |
| 2002/0006909 A1 | 1/2002 | Perlmutter et al. | 514/23 |
| 2002/0095135 A1 | 7/2002 | Meeker et al. | 604/522 |
| 2002/0115667 A1 | 8/2002 | Walkley et al. | 514/237.5 |

OTHER PUBLICATIONS

Asano et al., "Specific alpha galactosidase inhibitors, N–methylcalystegines—Structure/activity relationships of calystegines from Lycium chinense", Eur. J. Biochem., vol. 248: 296–303, 1997.

Bernotas et al., "Synthesis of (+)-1, 5–dideoxy–1,5–imino–D–galactitol, a potent alpha galactosidase inhibitor", Carbohydrate Res., vol. 167: 306–311, Sep. 1987.

Goldmann et al., "Biological Activities of the Nortropane Alkaloid, Calystegine B2, and Analogs: Structure Function Relationships", J. Natl. Prod., vol. 59, pp. 1137–1142, 1996.

Legler et al., "Synthesis of 5–Amino–5–Deoxy–D–Galactopyranose and 1,5–Dideoxy–1,5–Imino–D–Galactitol, and Their Inhibition of alpha nd beta–D–Galactosidases", Carbohydrate Research, vol. 155, pp. 119–129, Nov. 1986.

Tip W. Loo, et al., "Correction of Defective Protein Kinesis of Human P–glycoprotein Mutants by Substrates and Modulators", *The Journal of Biological Chemistry* 1997; vol. 272, No. 2, pp. 709–712.

C. Randall Brown, et al., "Chemical chaperones correct the mutant phenotype of the ΔF508 cystic fibrosis transmembrane conductance regulator protein", *Cell Stress & Chaperones* 1996; vol. 1 No. 2, pp. 117–125.

Ronald C. Rubenstein, et al., In Vitro Pharmacologic Restoration of CFTR–mediated Chloride Transport with Sodium 4–Phenylgutyrate in Cystic Fibrosis Epithelial Cells Containing ΔF508–CFTR, *Pharmacologic Correction of ΔF508–CFTR* 1997; vol. 100, No. 10, pp. 2457–2464.

Galina Kuznetsov, et al., "Folding of Secretory and Membrane Proteins", *The New England Journal of Medicine* 1998; vol. 339, No. 23, pp. 1688–1695.

F.M. Platt et al., "Prevention of lysosomal storage in Tay–Sachs mice treated with N–butyldeoxynojirimycin.", *Science* 1997; vol. 276, pp. 428–431.

T. Okumiya et al., "Galactose stabilizes various missense mutants of alpha–galactosidase in Fabry disease," *Biochem. Biophys. Res. Comm.* 1997; vol. 214, pp. 1219–1224.

Nakai Ansano et al., "Nitrogen–in–the–ring pyranoses and furanoses: structural basis of inhibiton of mammalian glycosidases," *J. Med. Chem.* 1994; vol. 37, pp. 3701.

Nakai Ansano et al., "Homojirimycin Isomers and Glycosides from *Aglaonema treubii*," *J. Nat. Prod.* 1997; vol. 60, pp. 98.

A. M Hurtley and A. Helenius, "Protein oligomerization in the endoplasmic reticulum," *Annu Rev Cell Biol*. 1989; vol. 5, pp. 277–307.

M.P. Dale et al., "Reversible inhibitors of beta–glucosidase," *Biochemistry* 1985; vol. 24, pp. 3530–3539.

Frances M. Platt, et al., "N–butyldeoxynojirimycin is a novel inhibitor of glycolipid biosynthesis," *J. Biol. Chem.* 1994; vol. 269, No. 11, pp. 8362–8365.

Frances M. Platt et al., "N–butyldeoxygalactonorjirimycin inhibits glycolilpid biosynthesis but does not affect n–linked oligosaccharide processing," *J. Biol. Chem.* 1994; vol. 269, No. 43, pp. 27108–27114.

Ishii et al., Biochem. Biophys. Res. Comm. 1993; 197(3):1585–89.

Okumiya e al., Biochem. Biophys. Res. Comm. 1995; 214(3): 1219–24.

Okumiya et al., Genetic Disease 1998; 2(1):76–82 (Japanese).

* cited by examiner

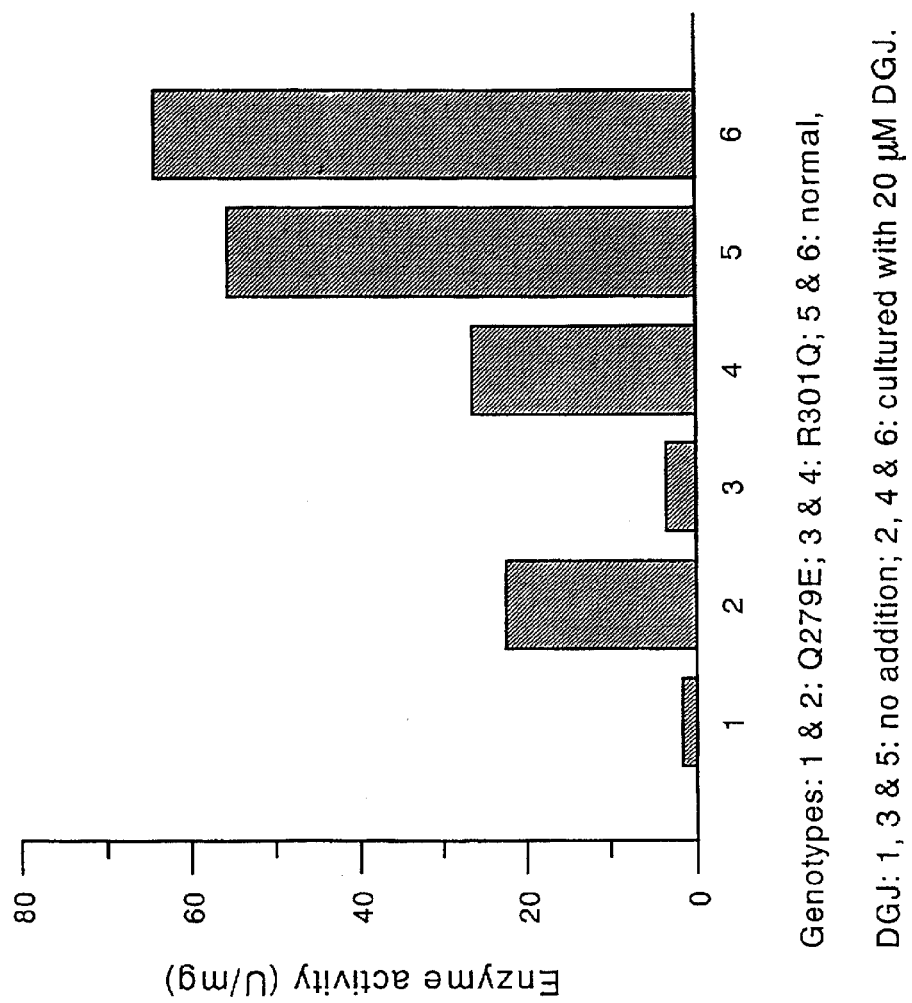

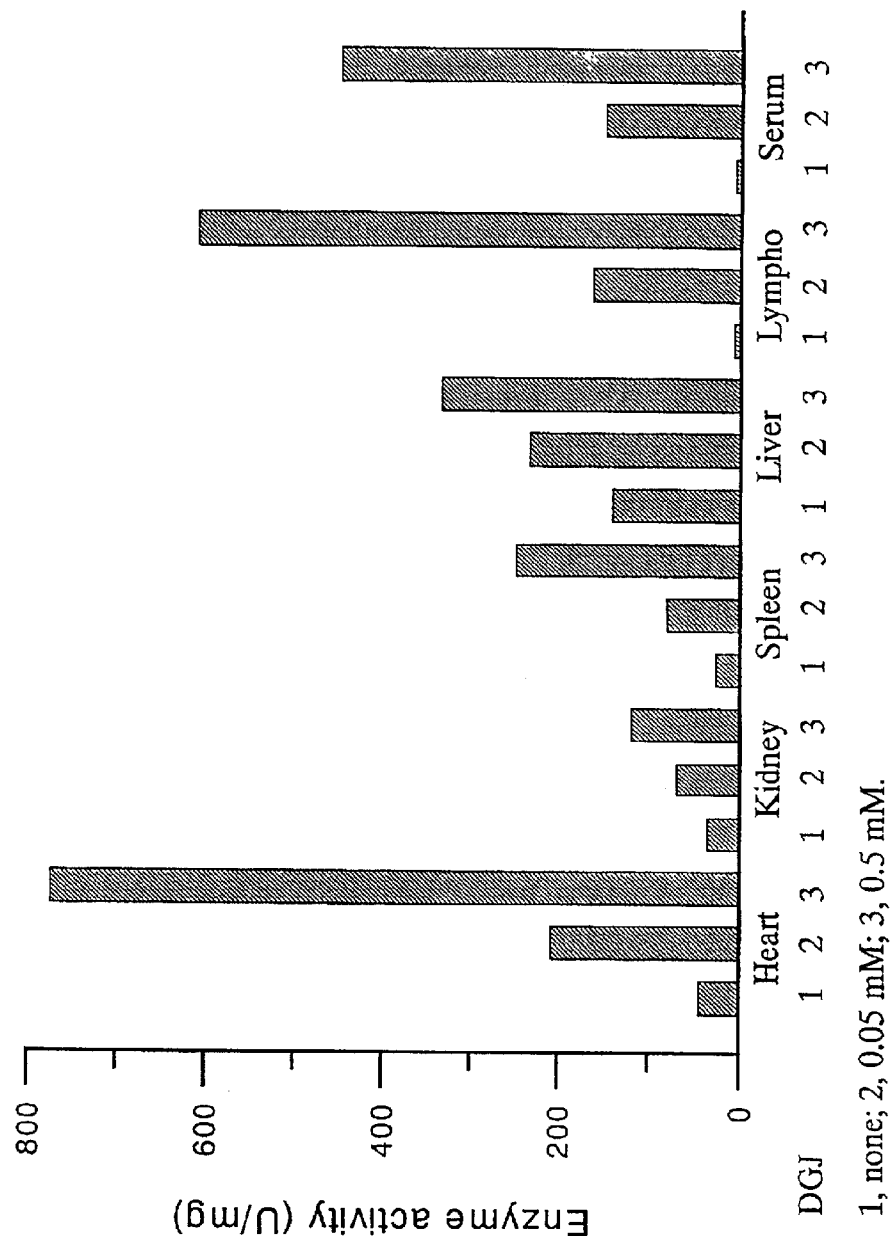

METHOD OF ENHANCING LYSOSOMAL α-GALACTOSIDASE A

This is a continuation of application Ser. No. 09/087,804, filed Jun. 1, 1998 now U.S. Pat. No. 6,274,597. This application is hereby incorporated herein by reference, in its entirety.

BACKGROUND OF THE INVENTION

1. Field of the Invention

This invention relates to a method of enhancing the activity of lysosomal α-Galactosidase A (α-Gal A) in mammalian cells and for treatment of glycosphingolipid storage diseases, in particular Fabry disease, by administration of 1-deoxy-galactonojirimycin and related compounds.

2. Background Information

Fabry disease (1) is a glycosphingolipid lysosomal storage disease caused by an X-linked inherited deficiency of lysosomal α-galactosidase A (α-Gal A), an enzyme responsible for the hydrolysis of terminal α-galactosyl residue from glycosphingolipids. A deficiency in the enzyme activity results in a progressive deposition of neutral glycosphingolipids, predominantly globotriaosylceramide (ceramide trihexoside, CTH), in vascular endothelial cells causing renal failure along with premature myocardial infarction and strokes in patients with this condition (2). This disorder is classified by clinical manifestations into two groups: a classic form with generalized vasculopathy and an atypical variant form, with clinical manifestations limited to heart. Recently, the atypical variant of the disease was found in 10% of adult male patients with unexplained left ventricular hypertrophy, increasing the estimation of frequency for the disorder (3). Like other glycosphingolipid lysosomal storage diseases, enzyme replacement therapy, gene therapy, bone marrow transplantation, and substrate deprivation are suggested as potential strategies for the treatment of this disease (4). However, at the moment the only treatment for this disorder is symptomatic management. Therefore, development of a new therapeutic strategy for this disease is urgently needed.

Studies (5) on residual α-Gal A activity of mutant enzymes revealed that some of mutant enzymes have similar kinetic properties to normal α-Gal A but with significant instability. This is considered as the case for most of atypical variant patients who generally showed higher residual α-Gal A activity than classical Fabry patients. For example (6), a purified mutant α-Gal A with a genotype of Q279E, found in a patient with atypical variant of Fabry disease, had the same Km and Vmax as the normal enzyme, but lost most of the enzyme activity by incubating the enzyme at pH 7.0 at 37° C. for 30 min while the normal enzyme was stable under the same condition. Both mutant and normal enzymes were stable at pH 5.0 at 37° C. Furthermore, the majority of the mutant enzyme protein in cells formed aggregate in endoplasmic reticulum (ER) and was quickly degraded (7), suggesting that the deficiency of the enzyme activity in this mutant maybe primarily caused by the unsuccessful exit of ER leading to excessive degradation of the enzyme protein. The present invention focuses on the aid of smooth escape of the enzyme from ER to prevent the degradation of the mutant enzyme.

SUMMARY OF THE INVENTION

The strategy of the invention is based on the following model. The mutant enzyme protein tends to fold in an incorrect conformation in ER where the pH is around 7. As a result, the enzyme is retarded from the normal transport pathway from ER through the Golgi apparatus and endosome to the lysosome, but instead is subjected to degradation. On the other hand, the enzyme protein with a proper conformation is transported to the lysosome smoothly and remains in an active form because the enzyme is more stable at a pH of less than 5. Therefore, a compound which is able to induce a proper conformation in mutant enzyme may serve as an enhancer for the enzyme. The present inventors have unexpectedly found that strong competitive inhibitors for α-Gal A at low concentrations enhance the mutant enzyme activity in cells, including mutant α-Gal A gene transfected COS-1 cells, fibroblasts from a transgenic mouse overexpressing mutant α-Gal A, and lymphoblasts from Fabry patients.

It is noted that while the above is believed to be the mechanism of operation of the present invention, the success of the invention is not dependent upon this being the correct mechanism.

Accordingly, it is one object of the present invention to provide a method of preventing degradation of mutant α-Gal A in mammalian cells, particularly in human cells.

It is a further object of the invention to provide a method of enhancing α-Gal A activity in mammalian cells, particularly in human cells. The methods of the present invention enhance the activity of both normal and mutant α-Gal A, particularly of mutant α-Gal A which is present in certain forms of Fabry disease.

In addition, the methods of the invention are also expected to be useful in nonmammalian cells, such as, for example, cultured insect cells and CHO cells which are used for production of α-Gal A for enzyme replacement therapy.

Compounds expected to be effective in the methods of the invention are galactose and glucose derivatives having a nitrogen replacing the oxygen in the ring, preferably galactose derivatives such as 1-deoxygalactonojirimycin and 3,4-diepi-α-homonojirimycin. By galactose derivative is intended to mean that the hydroxyl group at the C-3 position is equatorial and the hydroxyl group at the C-4 position is axial, as represented, for example, by the following structures:

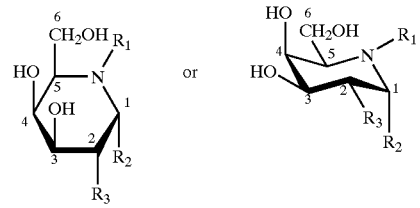

wherein $R_1$ represents H, methyl or ethyl; $R_2$ and $R_3$ independently represent H, OH, a simple sugar (e.g. —O—galactose), a 1-3 carbon alkyl, alkoxy or hydroxyalkyl group (e.g. $CH_2OH$).

Other specific competitive inhibitors for (x-galactosidase, such as for example, calystegine $A_3$, $B_2$ and $B_3$, and N-methyl derivatives of these compounds should also be useful in the methods of the invention. The calystegine compounds can be represented by the formula

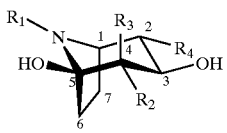

wherein for calystegine $A_3$: $R_1$=H, $R_2$=OH, $R_3$=H, $R_4$=H; for calystegine $B_2$: $R_1$=H, $R_2$=OH, $R_3$=H, $R_4$=OH; for calystegine $B_3$: $R_1$=H, $R_2$=H, $R_3$=OH, $R_4$=OH; for N-methyl-calystegine $A_3$: $R_1$=$CH_3$, $R_2$=OH, $R_3$=H, $R_4$=H; for N-methyl-calystegine $B_2$: $R_1$=$CH_3$, $R_2$=OH, $R_3$=H, $R_4$=OH; and for N-methyl-calystegine $B_3$: $R_1$=$CH_3$, $R_2$=H, $R_3$=OH, $R_4$=OH.

It is yet a further object of the invention to provide a method of treatment for patients with Fabry disease. Administration of a pharmaceutically effective amount of a compound of formula

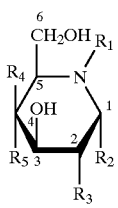

wherein $R_1$ represents H, $CH_3$ or $CH_3CH_2$;

$R_2$ and $R_3$ independently represent H, OH, a 1-6 carbon alkyl, hydroxyalkyl or alkoxy group (preferably 1-3), or a simple sugar;

$R_4$ and $R_5$ independently represent H or OH; or a compound selected from the group consisting of 2,5-dideoxy-2,5-imino-D-mannitol, α-homonojirimycin, 3,4-diepi-α-homonojirimycin, 5—O—α-D-galactopyranosyl-α-homonojirimycin, 1-deoxygalactonojirimycin, 4-epi-fagomine, and 1-Deoxy-nojirimycin and their N-alkyl derivatives, will alleviate the symptoms of Fabry disease by increasing the activity of mutant α-Gal A in patients suffering from Fabry disease. Other competitive inhibitors of α-Gal A, such as calystegine compounds and derivatives thereof should also be useful for treating Fabry disease.

Persons of skill in the art will understand that an effective amount of the compounds used in the methods of the invention can be determined by routine experimentation, but is expected to be an amount resulting in serum levels between 0.01 and 100 μM, preferably between 0.01 and 10 μM, most preferably between 0.05 and 1 μM. The effective dose of the compounds is expected to be between 0.5 and 1000 mg/kg body weight per day, preferably between 0.5 and 100, most preferably between 1 and 50 mg/kg body weight per day. The compounds can be administered alone or optionally along with pharmaceutically acceptable carriers and excipients, in preformulated dosages. The administration of an effective amount of the compound will result in an increase in α-Gal A activity of the cells of a patient sufficient to improve the symptoms of the patient. It is expected that an enzyme activity level of 30% of normal could significatly improve the symptoms in Fabry patients, because the low range of enzyme activity found in apparently normal persons is about 30% of the average value (2).

Compounds disclosed herein and other competitive inhibitors for α-Gal A which will be known to those of skill in the art will be useful according to the invention in methods of enhancing the intracellular activity of α-Gal A and treating Fabry disease.

BRIEF DESCRIPTION OF THE DRAWINGS

FIGS. 2A–2B. Enhancement of α-Gal A by DGJ in fibroblasts derived from Tg mice (2A) and lymphoblasts derived from Fabry patients (2B).

FIG. 11. Enhancement of α-Gal A activity by administration of DGJ to TgM mice. DGJ solutions (0.05 mM or 0.5 mM) were placed as drink sources for TgM mice (four mice as a group). After 1 week administration, the organs were homogenized for the determination of the enzyme activity. The data were the subtraction of endogenous mouse α-Gal A activity obtained from non-Tg mice feeding with DGJ from the activity of TgM mice. The enzyme activities presented were the mean values and the standard deviations were less than 10%.

DETAILED DESCRIPTION OF THE INVENTION

Abbreviations

Figure 1:
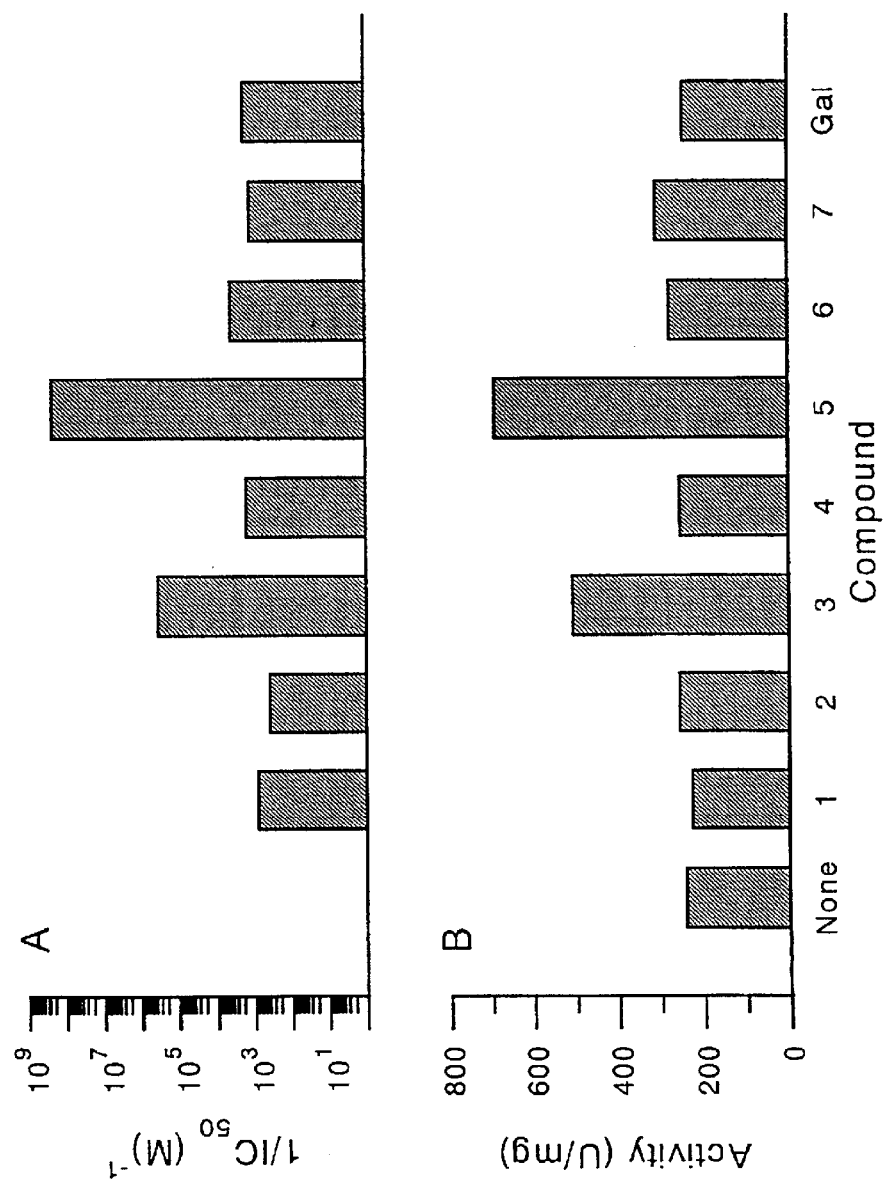
FIGS. 1A–1C. In vitro inhibition (1A) and intracellular enhancement (1B and 1C) of α-Gal A by alkaloid compounds. The alkaloid compounds used were: (1) 2,5-Dideoxy-2,5-imino-D-mannitol, (2) α-Homonojirimycin, (3) 3,4-Diepi-α-homonojirimycin, (4) 5—O—α-D-Galactopyranosyl-α-homonojirimycin, (5) 1-deoxygalactonojirimycin, (6) 4-epi-Fagomine, (7) 1-Deoxy-nojirimycin, (Gal) Galactose. The intracellular α-Gal A activity in COS-1 cells transfected by cDNA of a mutant α-Gal A (R301Q) was assayed as described in "Methods". (A) The inhibition assay was performed under the Methods. $IC_{50}$'s of the compounds were 1.3 mM (1), 2.6 mM (2), 2.9 μM (3), 0.62 mM (4), 4.7 nM (5), 0.25 mM (6), 0.8 mM (7), and 24 mM (Gal, galactose), respectively.

Abbreviations used herein are set forth below for convenience: α-Gal A, human lysosomal α-galactosidase A; TgN mouse, a transgenic mouse overexpressing normal human lysosomal α-galactosidase A; TgM mouse, a transgenic mouse overexpressing a mutant human lysosomal α-galactosidase A with a single amino acid replacement of Arg at 301 position by Gln (R301Q); TgN fibroblast, fibroblast generated from a TgN mouse; TgM fibroblast, fibroblast generated from a TgM mouse; DGJ, 1-deoxy-galactonojirimycin; DE-HNJ, 3,4-di-epi-(α-homonojirimycin; pNP-α-Gal, p-nitrophenyl-α-D-galactoside; 4-mU-α-Gal, 4-methylumbelliferyl-α-D-galactoside; FCS, fetal calf serum; PBS, phosphate-buffered saline; BSA, bovine serum albumin; TLC, thin-layer chromatography; CTH, globotriaosylceramide or ceramide trihexoside; CDH, ceramide dihexoside; CMH, ceramide monohexoside; ER, endoplasmic reticulum.

Materials and Methods

Materials. Alkaloidal compounds were either purified from plants or partial chemical modified derivatives of the plant products (9). TgN and TgM mice were generated as previously reported (10, 11). TgN or TgM fibroblasts were established from TgN or TgM mouse as routine. Human lymphoblasts were Epstein-Barr virus-transformed lymphoblast lines from a normal adult or patients with Fabry disease (6). Normal and mutant α-Gal A cDNAs for transient express in COS-1 cells were cloned as reported (12). α-Gal A for in vitro inhibition study of alkaloids was expressed and purified from the culture medium of Sf-9 cells infected by a recombinant baculovirus encoded normal α-Gal A gene (13). [$^{14}$C]-CTH was prepared by a combination of chemical and sphingolipid ceramide N-deacylase reactions (14).

Methods

Cell culture. COS-1 cells, TgN and TgM fibroblasts were cultured in Ham's F-10 medium supplemented with 10% FCS and antibiotics. Lymphoblasts were cultured in RPMI-1640 with 10% FCS and antibiotics. All cell cultures were carried out at 37° C. under 5% $CO_2$. As a model for fibroblasts and lymphoblasts, cells (3x105 for fibroblasts and 5×10$^5$ for lymphoblasts) were cultured in 10 ml of the preferred medium with or without DGJ at 20 μM for 4 days before taken to the assay for intracellular enzyme activity.

Transient expression of α-Gal A in COS-1 cells. COS-1 cells (5×10$^5$) were transfected with 1 μg of plasmid DNA and 8 μl Lipofectamine (Gibco, Gaithersburg, Md. U.S.A.) in 1.2 ml Opti-MEM medium (Gibco) per 60-mm dish. After incubating at 37° C. for 6 hr, 1.2 ml of the same medium containing 20% FCS was added and the culture was incubated overnight. After replacing the medium with 2.4 ml complete Ham's F-10 medium, alkaloid was added at an appropriate concentration, and further incubated for 1 day, before taken to the assay for intracellular enzyme activity.

Intracellular enzyme assay for α-Gal A. After washing with phosphate-buffered saline twice, the cells were homogenized in 200 μl of $H_2O$, and 10 μl of the supernatant obtained by centrifugation at 10,000×g was incubated at 37° C. with 50 μl of the substrate solution composed by 6 mM 4-mU-α-Gal and 90 mM N-acetylgalactosamine in 0.1 M citrate buffer (pH 4.5) for the enzyme assay. All the data are the averages of triplicate measurements with standard deviation less than 10%. One unit of enzyme activity was defined as one muol of 4-methylumbelliferone released per hour at 37° C.

In vitro inhibition assay of α-Gal A. The enzyme activity was assayed with pNP-α-Gal as substrate. A typical inhibition reaction was performed in a mixture of 200 nmol pNP-α-Gal, appropriate enzyme and inhibitor in a total volume of 120 μl with 0.05 M citrate buffer (pH 4.5). After incubation at 37° C. for 15 min, the reaction was terminated by addition of 1 ml of 0.2 M borate buffer (pH 9.8), and the amount of pNP released was measured as the absorbance at 490 nm.

EXAMPLE 1

A series of plant alkaloids (Scheme 1, ref. 9) were used for both in vitro inhibition and intracellular enhancement studies of α-Gal A activity. The results of inhibition experiments are shown in FIG. 1A.

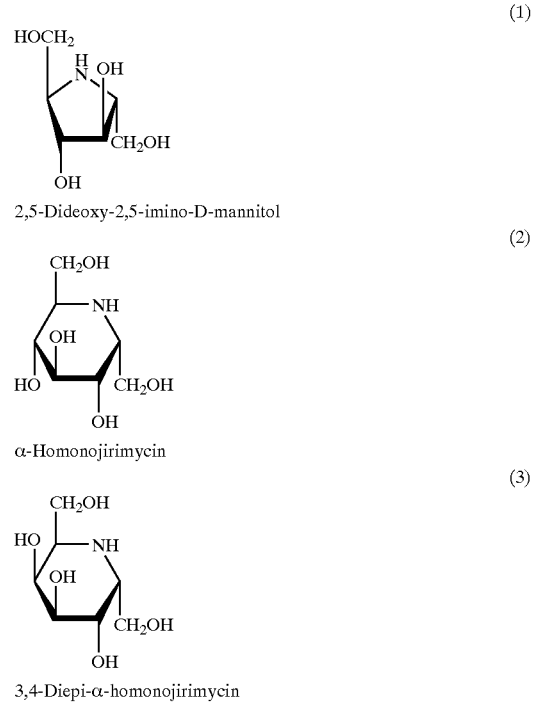

(4)

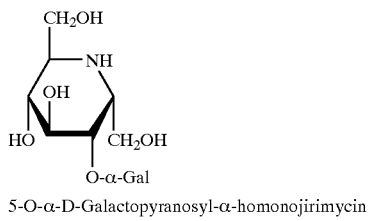

5-O-α-D-Galactopyranosyl-α-homonojirimycin (5)

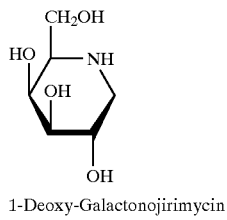

1-Deoxy-Galactonojirimycin (6)

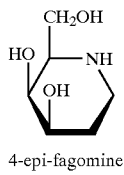

4-epi-fagomine (7)

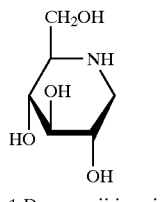

1-Deoxy-nojirimycin

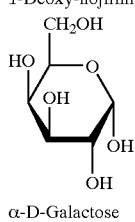

α-D-Galactose

Figure 1C:
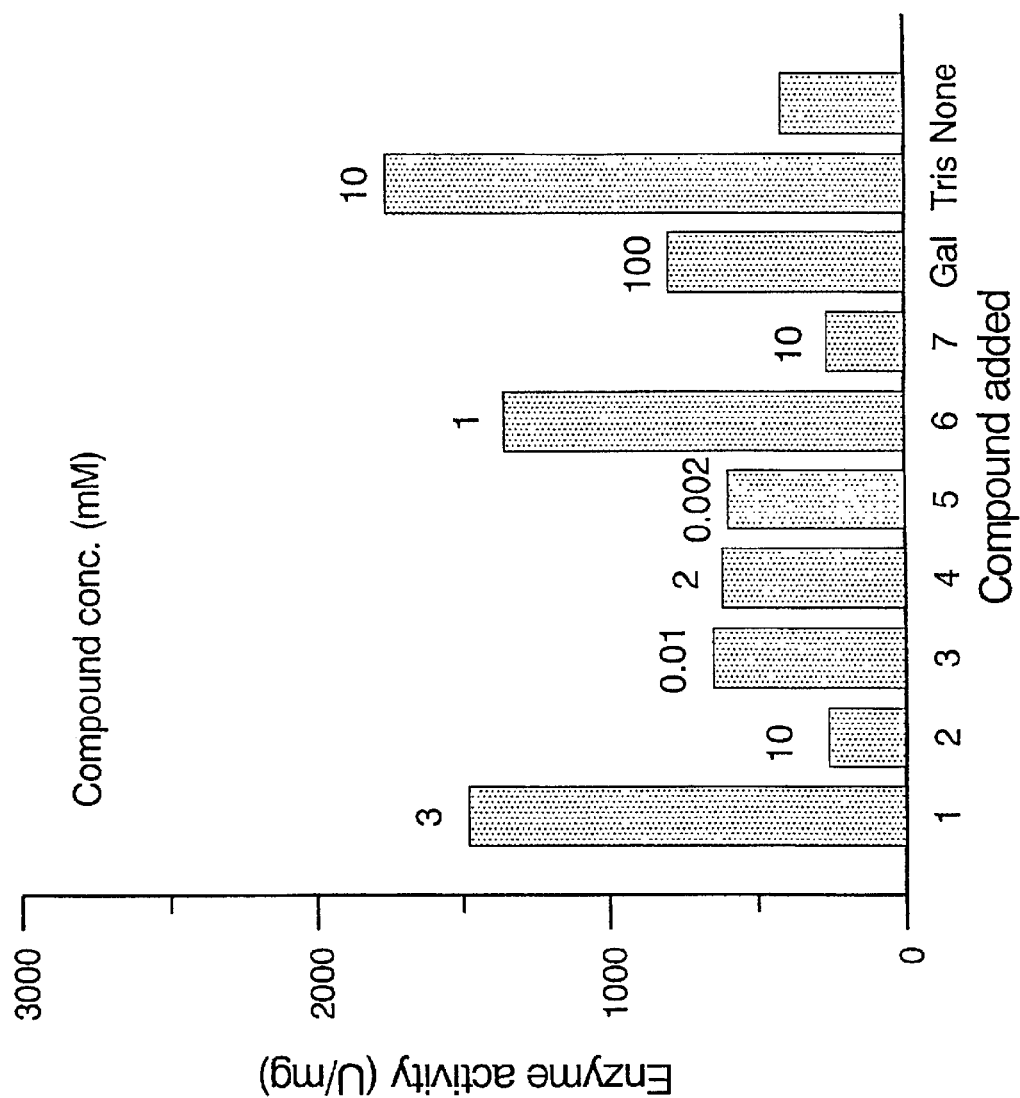

Among the tested compounds, 1-deoxy-galactonojirimycin (DGJ, 5) known as a powerful competitive inhibitor for α-Gal A, showed the highest inhibitory activity with $IC_{50}$ at 4.7 nM. α-3,4-Di-epi-homonojirimycin (3) was an effective inhibitor with $IC_{50}$ at 2.9 μM. Other compounds showed moderate inhibitory activity with $IC_{50}$ ranging from 0.25 mM (6) to 2.6 mM (2). Surprisingly, these compounds also effectively enhanced α-Gal A activity in COS-1 cells transfected with a mutant α-Gal A gene (R310Q), identified from an atypical variant form of Fabry disease with a residual α-Gal A activity at 4% of normal. By culturing the transfected COS-1 cells with these compounds at concentrations cat 3-10-fold of $IC_{50}$ of the inhibitors, α-Gal A activity was enhanced 1.5–4-fold (FIG. 1C). The effectiveness of intracellular enhancement paralleled with in vitro inhibitory activity while the compounds were added to the culture medium at 10 μM concentration (FIG. 1B).

EXAMPLE 2

Figure 2A:
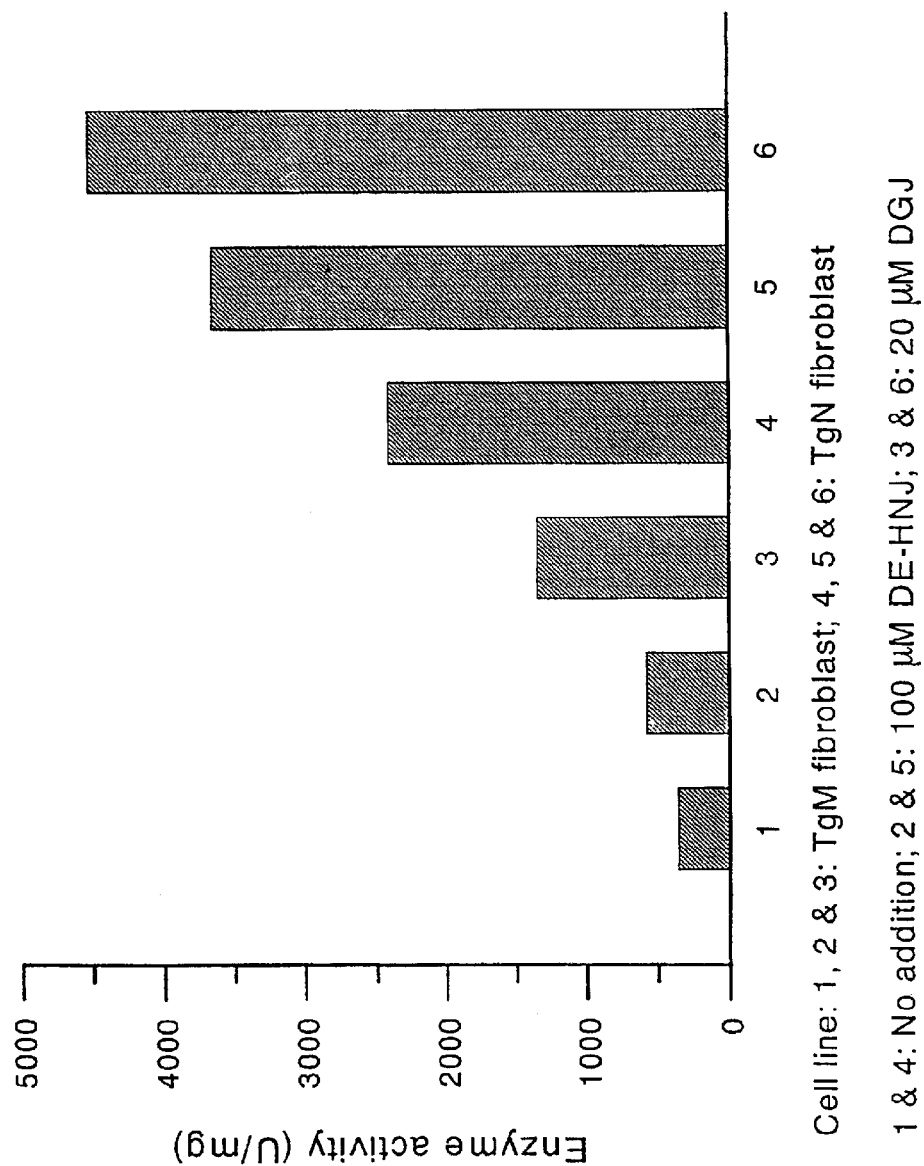

DGJ, the strongest inhibitor in vitro and most effective intracellular enhancer, was chosen for more detailed characterization. DGJ was added to the TgM or TgN fibroblasts (FIG. 2A) and lymphoblasts derived from Fabry patients with genotypes of R301Q or Q279E mutations (FIG. 2B). The enzyme activity found in TgM fibroblasts increased 6-fold by co-cultivation with 20 μM DGJ and reached 52% of normal. The DGJ also showed a similar effect on lymphoblasts in which the residual enzyme activity was enhanced by 8- and 7-fold in R301Q and Q279E, i.e., 48% and 45% of normal. The enzyme activity in Tg normal (TgN) fibroblasts and normal lymphoblasts also showed an increase by cultivation with DGJ.

EXAMPLE 3

Figure 3:
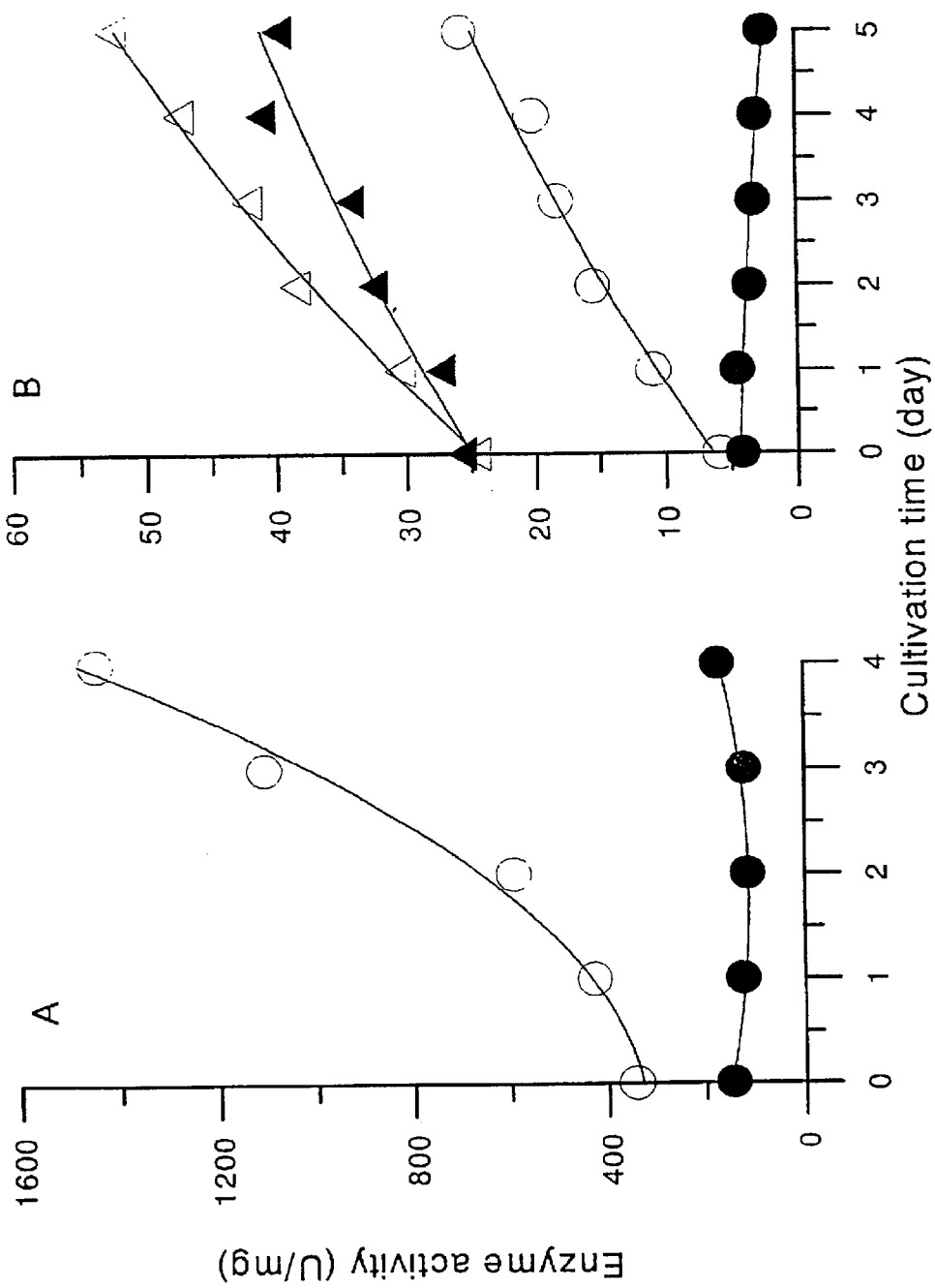
FIG. 3. Time courses of enhancement of α-Gal A by DGJ in TgM fibroblasts (A) and lymphoblasts (B). The cell cultures were performed under the Methods section. DGJ concentration added was 20 μM. The genotype of the human lymphoblasts was R301Q. ●, mutant cell cultured without DGJ; ○, mutant cell cultured with DGJ; ▲, normal lymphoblast cultured without DGJ; Δ, normal lymphoblast cultured with DGJ.

The TgM fibroblasts and human lymphoblasts of normal and patient with a mutation on R301Q were cultured in the presence of DGJ at 20 μM. In the cultures without DGJ, the α-Gal A activity in TgM fibroblasts or mutant lymphoblasts was unchanged (FIG. 3). However, by including DGJ, the enzyme activity showed significantly increase in these cell cultures. The enzyme activity in mutant lymphoblasts reached to 64% of those found in normal lymphoblasts cultured without DGJ at the fifth day. The enzyme activity in normal lymphoblasts was also enhanced 30% after cultivation with DGJ.

EXAMPLE 4

DGJ concentration dependence of α-Gal A enhancement in transfected COS-1 cells, TgM fibroblasts and lymphoblasts with a phenotype of R301Q was examined.

Figure 4:
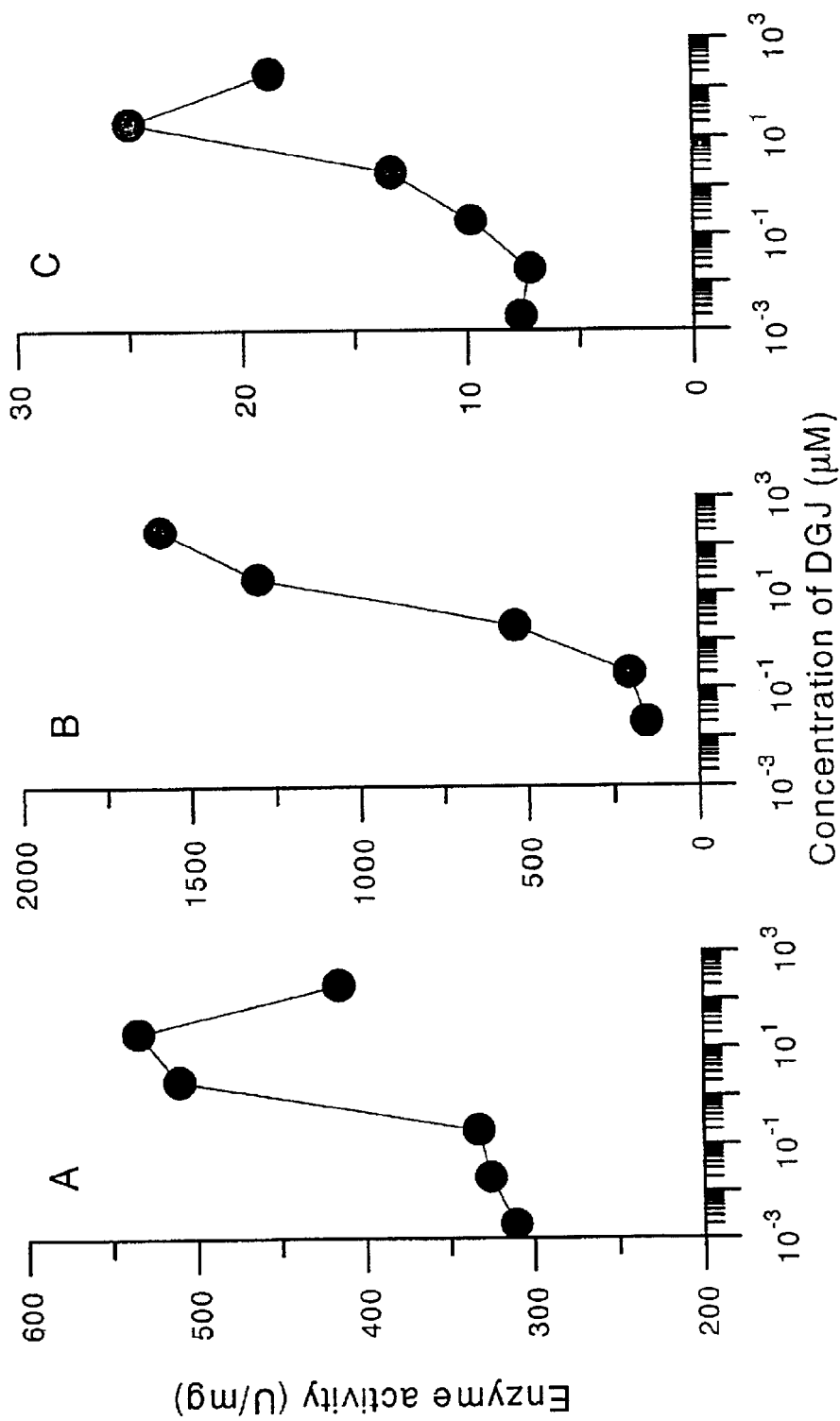
FIG. 4. DGJ concentration dependence of α-Gal A enhancement in transfected COS-1 cells (A), TgM fibroblasts (B) and lymphoblasts with a genotype of R301Q (C). The cells were cultured at 37° C. in Ham's F-10 medium (COS-1 cells, TgM fibroblasts) or RPMI-1640 medium supplemented with 10% FCS (lymphoblasts) containing DGJ at a variable concentration for 4 days. The cDNA transfected into COS-1 cells encoded a mutant α-Gal A (R301Q).

As shown in FIG. 4, the enzyme activity increased with the increase in the concentration of DGJ in the range of 0.2–20 μM in transfected COS-1 cells (FIG. 4A) and lymphoblasts (FIG. 4C), and between 0.2–200 μM in TgM fibroblasts (FIG. 4B), respectively. A higher concentration of DGJ suppressed the enhancement effect.

Figure 5:
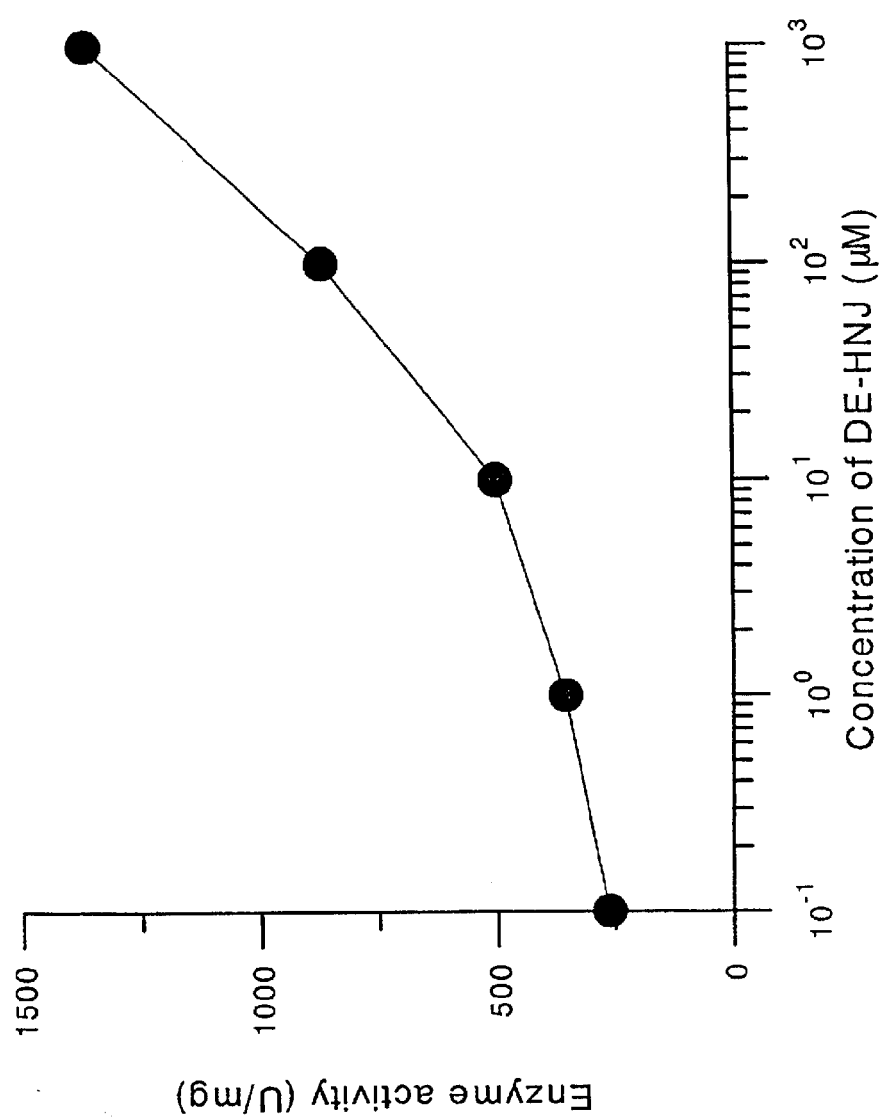
FIG. 5. DE-HNJ concentration dependence of α-Gal A enhancement in transfected COS-1 cells.

DE-HNJ showed the same effect on the enhancement of α-Gal A in COS-1 cells transfected with a mutant cDNA of the enzyme (R301Q) at the higher concentrations (1–1000 μM) compared with DGJ (FIG. 5). It is clear that DE-HNJ at 1 mM in culture medium did not inhibit intracellular enzyme activity of COS-1 cells.

EXAMPLE 5

Figure 6:
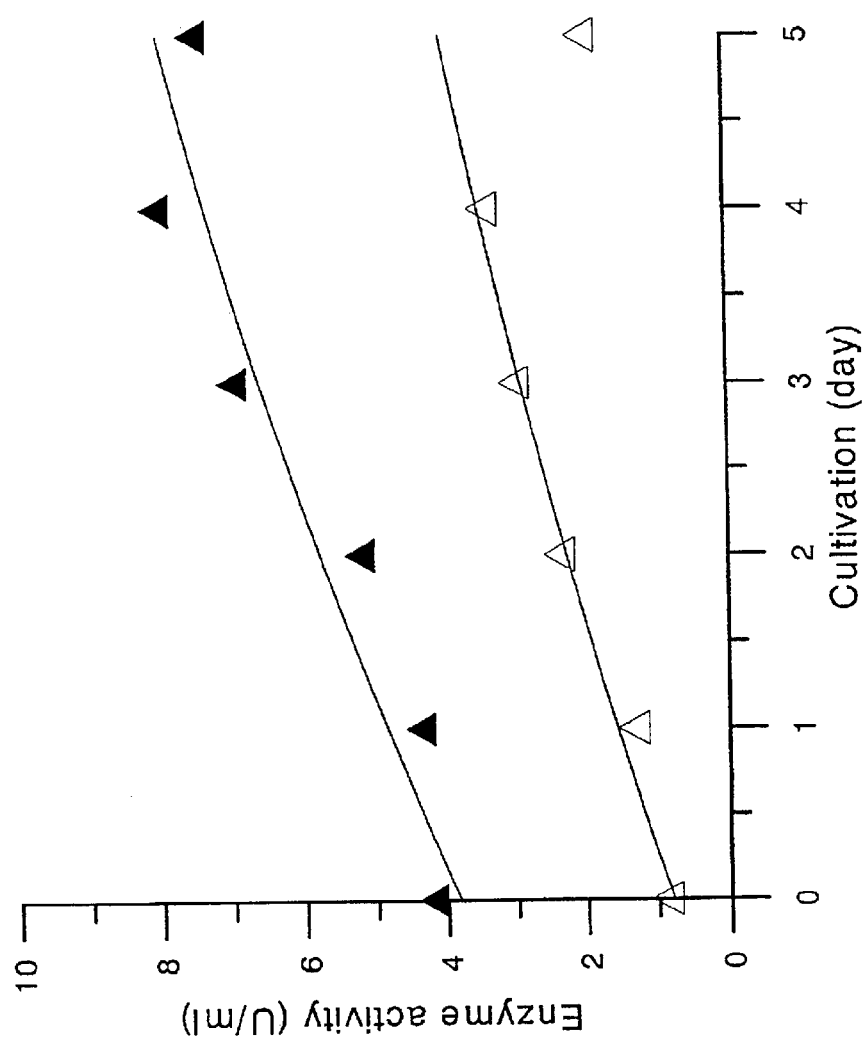
FIG. 6. Stabilization of DGJ enhanced α-Gal A in lymphoblasts. Δ, R301Q lymphoblasts cultivated without DGJ; ▲, R301Q lymphoblasts cultivated with DGJ.

FIG. 6 shows an experiment to measure stabilization of DGJ enhanced α-Gal A in lymphoblasts. The cells were cultured at 37° C. in 10 ml RPMI-1640 medium supplemented with 10% FCS containing DGJ at 20 μM for 4 days, and $5 \times 10^5$ cells were transferred to 13 ml of RPMI1640 with 10% FCS without DGJ. Two ml of the medium was taken each day for the enzyme assay. The initial surplus of the total α-Gal A activity between pre-cultivation with and without DGJ was maintained for 5 days after replacement of the medium without DGJ (FIG. 6), suggesting that the enhanced enzyme is stable in the cells for at least 5 days.

EXAMPLE 6

To study the functioning of the enhanced enzyme in the cells, [$^{14}$C]-CTH was loaded to the culture of TgN fibroblasts.

Figure 7:
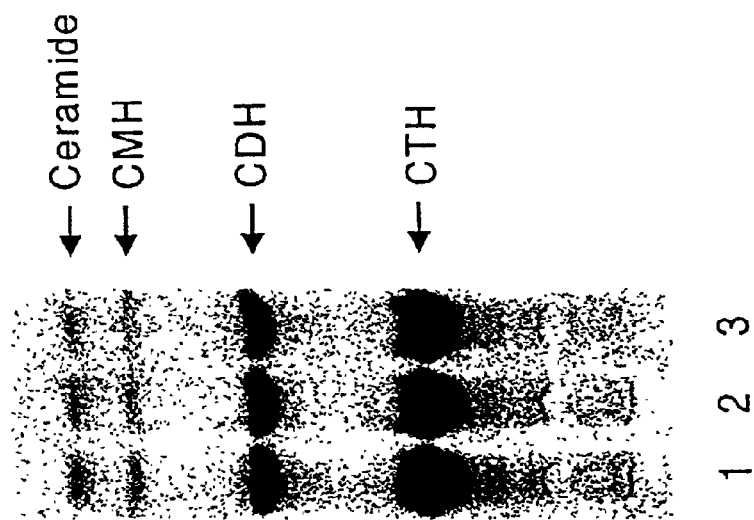
FIG. 7. TLC analysis of metabolism of [$^{14}$C]-CTH in TgN fibroblasts cultured with DGJ. The TgN fibroblasts were cultured at 37° C. in Ham's F-10 medium-10% FCS containing DGJ at 0 (lane 1), 2 (lane 2) and 20 μM (lane 3) for 4 days. After washing with the medium without DGJ, [$^{14}$C]-CTH (200,000 cpm) in 2.5 ml of Opti-MEM medium (Gibco, Gaithersburg, Md. U.S.A.) was added to the cells, and incubated for 5 hr. The cells were washed with 2 ml of 1% BSA and 2 ml of PBS three times each. The neutral glycolipids were extracted by $CHCl_3$: MeOH (2:1), and purified by mild alkaline treatment, extraction with MeOH:n-hexane (1:1) and Folch extraction (19).

The determination of glycolipid was performed by thin-layer chromatography using $CHCl_3$:MeOH:$H_2O$ (65:25:4) as a developing solvent, and visualized by a Fuji-BAS imaging system (FIG. 7). The amount of ceramide di-hexoside (CDH), a metabolic product of CTH by α-Gal A, was comparable between the cells cultivated with 20 μM DGJ and without DGJ (4.5% vs. 4.3% of the total neutral glycolipids), indicating that the intracellular enzyme is not inhibited by DGJ at the concentration used.

EXAMPLE 7

In order to determine whether DGJ affects the biosynthesis of α-Gal A, the level of α-Gal A mRNA in mutant lymphoblasts (R301Q) cultured with DGJ were measured by a competitive polymerase chain reaction (PCR) method (15). FIG. 8A clearly shows that the mRNA of α-Gal A was unchanged by cultivation of lymphoblasts with 50 μM of DGJ.

On the other hand, Western blot analysis indicated a significant increase of the enzyme protein in TgM fibroblasts, and the increase corresponded to the concentration of DGJ (FIG. 8B). More enzyme protein with lower molecular weight (ca. 46 kD) in the cells cultivated with DGJ suggested the higher level of matured enzyme (16). These results indicate that the effect of DGJ on enhancement of the enzyme is a post-transcriptional event.

EXAMPLE 8

Figure 8:
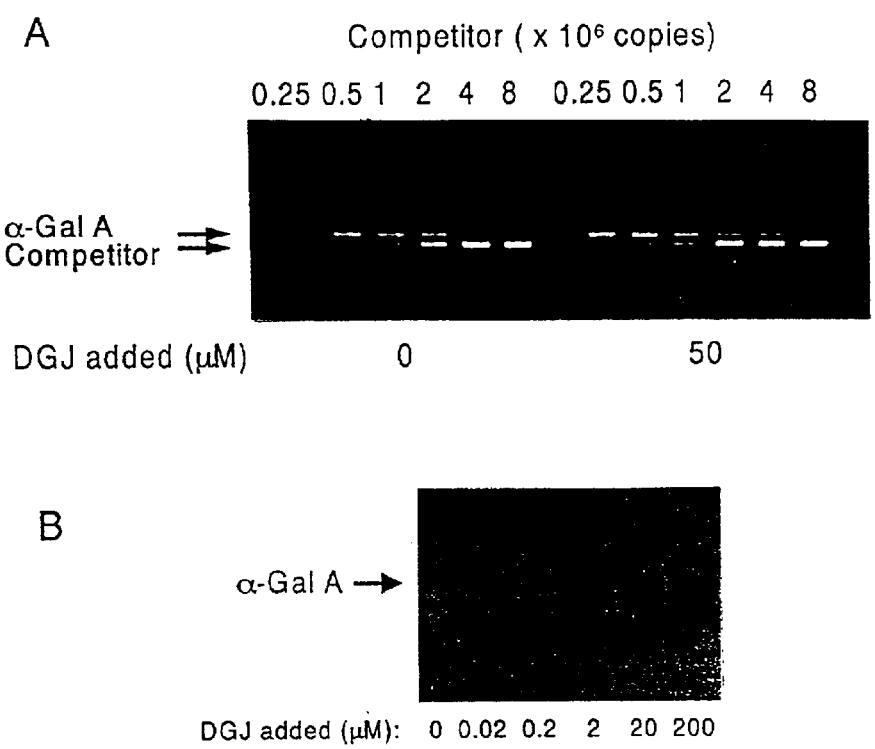
FIG. 8A. Determination of mRNA of ax-Gal A in mutant lymphoblasts (R301Q) cultured with DGJ. The human mutant lymphoblasts (R301Q) were cultured with or without 50 μM DGJ for 4 days. The mRNAs of α-Gal A were determined by a compeititve RT-PCR method (15).
FIG. 8B. Western blot of mutant α-Gal A (R301Q) expressed in TgM fibroblasts. The supernatant of cell homogenate containing 10 μg protein was applied to SDS-PAGE, and Western blot was performed with an anti-α-Gal A antibody raised in rabbit.
Figure 9:
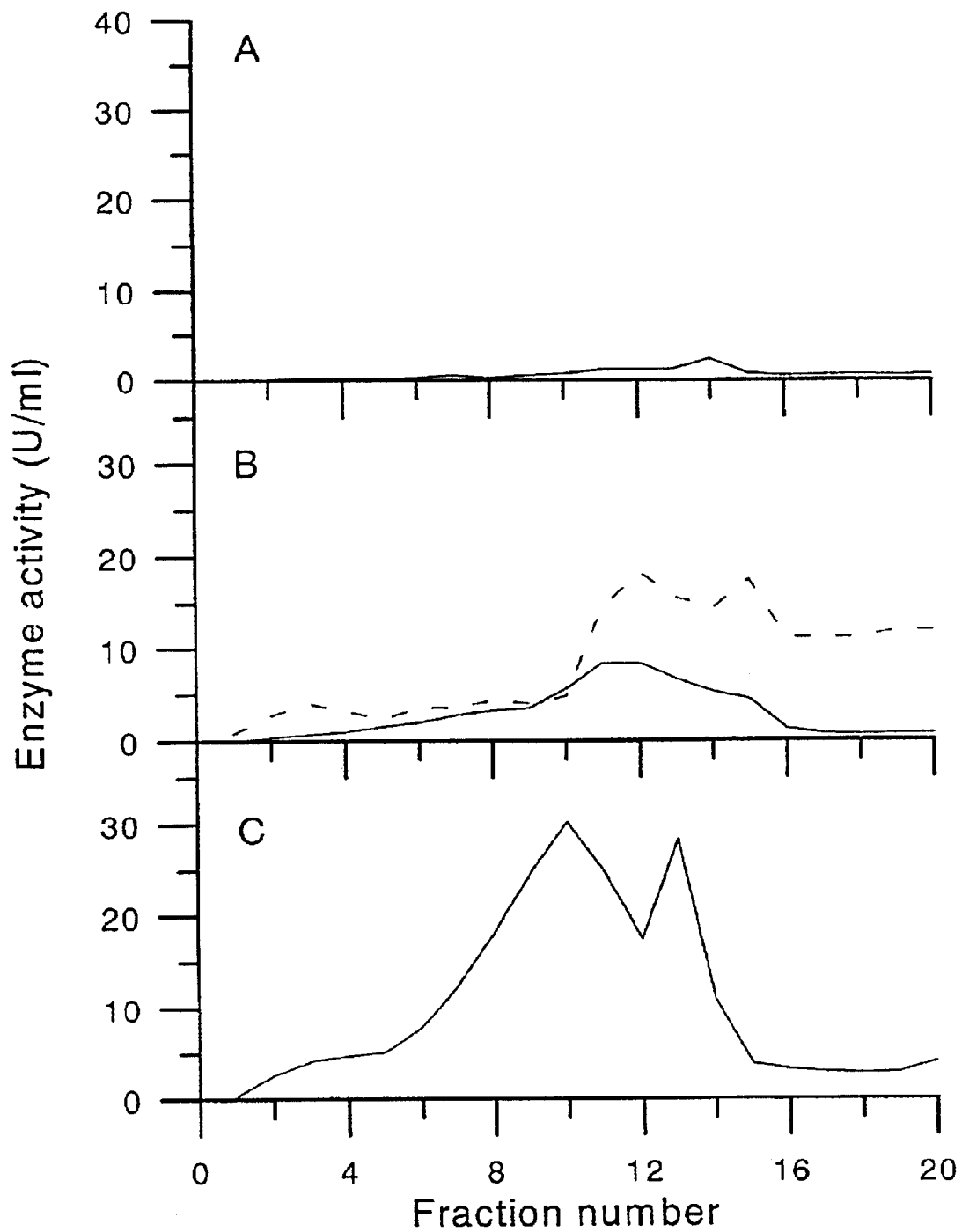
FIG. 9. Percoll density-gradient centrifugation with TgM fibroblasts (A), TgM fibroblasts cultured with 20 μM DGJ (B), and TgN fibroblasts (C). The Percoll density-gradient centrifugation was performed with density markers (Sigma Chemical Co., St. Louis, Mo., U.S.A.) as previously described by Oshima et al. (8). β-Hexosaminidase, a lysosomal marker enzyme, was assayed with 4-methylumbelliferyl-β-N-actyl-D-glucosamine as substrate. Solid line, α-Gal A activity; broken line, β-hexosaminidase activity.

To confirm the enhanced enzyme is transported to the lysosome, a sub-cellular fractionation was performed with Tg mice fibroblasts (FIG. 8). The overall enzyme activity in TgM fibroblasts was lower and eluted with a density marker of 1.042 g/ml which contained Golgi apparants fractions (20) (FIG. 9A). By cultivation with 20 μM DGJ, the enzyme activity in TgM fibroblasts showed higher overall enzyme activity and the majority of the enzyme eluted with the same fraction of a lysosomal marker enzyme, β-hexosaminidase (FIG. 9B). The elution pattern of (x-Gal A activity in TgM was also changed to those found in TgN fibroblasts (FIG. 9C).

EXAMPLE 9

Figure 10:
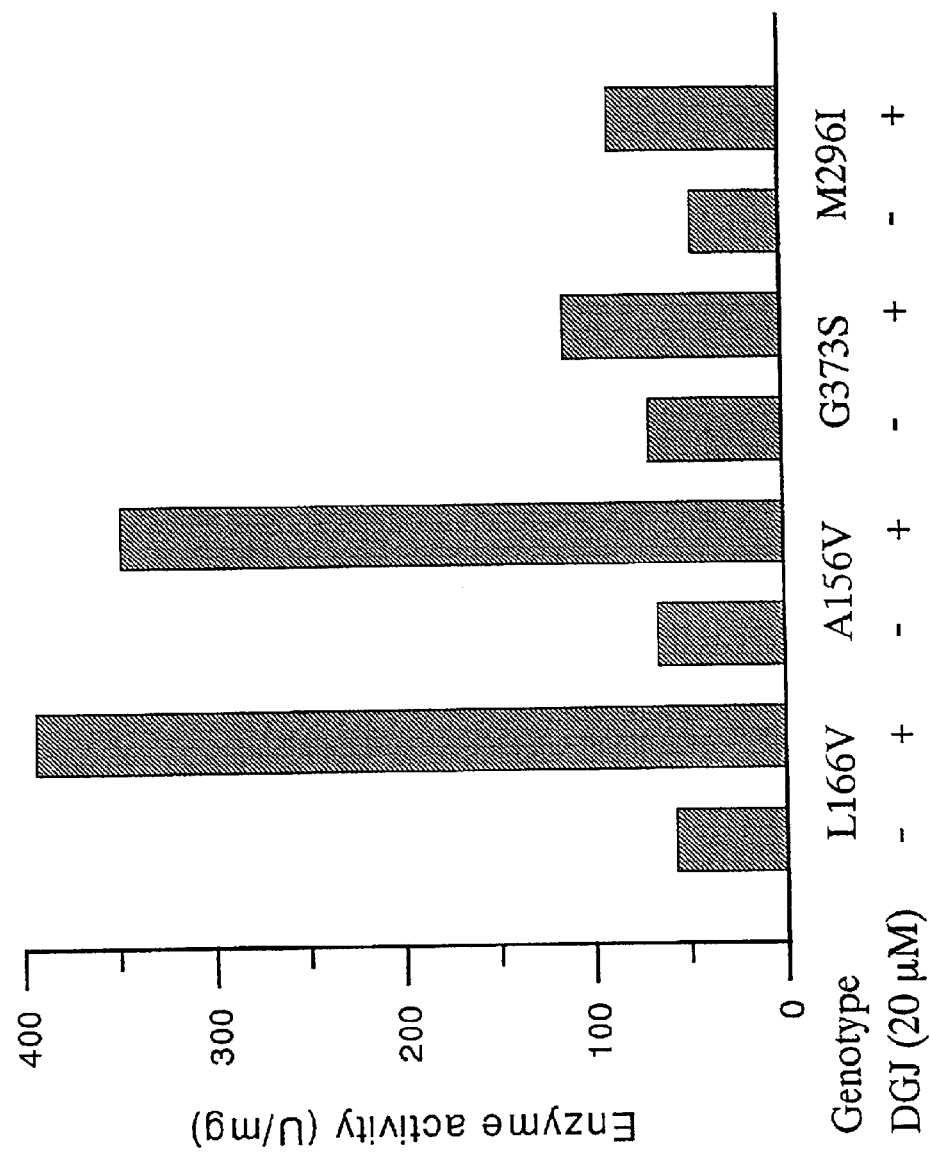
FIG. 10. Enhancement of α-Gal A in transfected COS-1 cells by DGJ. The cDNA's transfected to COS-1 cells were α-Gal A's with the mutations on L166V, A156V, G373S and M296I. DGJ concentration added was 20 μM.

The genotypes of R301Q and Q279E were found from patients with atypical type of Fabry disease. The effectiveness of DGJ on enhancement of α-Gal A activity was examined with other genotypes and phenotypes of Fabry disease. In this experiment, three mutant α-Gal A cDNA's, L166V, A156V and G373S found in patients with classical type of Fabry disease and a mutation of M296I found from patients with atypical form of the disease were used. FIG. 10 shows that the inclusion of DGJ increased enzyme activity in all four genotypes tested, especially for L166V (7-fold increase) and A156V (5-fold increase). The data indicated that this approach is useful not only for the atypical form, but also classical form of the disease.

EXAMPLE 10

DGJ was administrated to Tg mice by feeding 0.05 or 0.5 mM DGJ solutions as drinking source for a week corresponding to the dosage of DGJ at approximate 3 or 30 mg per kilogram of body weight per day. The enzyme activity was elevated 4.8- and 18-fold in heart, 2.0- and 3.4-fold in kidney, 3.1- and 9.5-fold in spleen and 1.7- and 2.4-fold in liver, respectively (FIG. 11). The increase of the enzyme activity in organs responded to the increase of DGJ dosage. Since the mutant gene (R301Q) was found in atypical variant type Fabry patients which have clinical symptoms limited to heart, the fact that oral adiministration of DGJ specifically enhances the α-Gal A activity in the heart of TgM mouse is particularly significant.

DISCUSSION

It is known that the ER possesses an efficient quality control system to ensure that transport to the Golgi complex is limited to properly folded and assembled proteins, and the main process of the quality control is enforced by a variety of chaperons (17). One explanation of the results presented in the present application is as follows: In some phenotypes of Fabry disease, the mutation causes imperfect, but flexible folding of the enzyme, while the catalytic center remains intact. Inhibitors usually have high affinity to the enzyme catalytic center, and the presence of the inhibitor affixes the enzyme catalytic center and reduces the flexibility of folding, perhaps leading to the "proper" conformation of the enzyme. As a result, the enzyme could be passed through the "quality control system", and transported to Golgi complex to reach maturation. Once the enzyme is transported to lysosome where the pH is acidic, the enzyme tends to be stable with the same conformation, because the enzyme is stable under the acidic condition (6). In such cases, the inhibitor acts as chaperon to force the enzyme to assume the proper conformation. We propose to use "chemical chaperon" as a term for such low molecular weight chemical with such functions.

It is crucial for the functioning of the enzyme that the smooth dissociation of the compound from the enzyme catalytic center in lysosome could be taken. Since the compounds used in this study are competitive inhibitors, the dissociation of the inhibitors depends upon two factors: (i) the inhibitor concentration, and (ii) pH. Dale et al. (18) have shown that binding of 1-deoxynojirimycin to α-glucosidase is pH dependent where the inhibitor bound to the enzyme 80-fold more tightly at pH 6.5 compared to pH 4.5, suggesting that the nojirimycin derivatives function as an unprotonated form. This may explain the results on the functioning of α-Gal A in cells shown in FIG. 7, because the inhibitor can bind to the enzyme at neutral condition, and release from the enzyme at the acidic condition where DGJ tends to be protonated.

The results described herein show that DGJ can effectively enhance mutant α-Gal A activities in lymphoblasts of patients with atypical variant of Fabry disease with genotypes of R301Q and Q279E. The effectiveness of DGJ on other phenotypes of Fabry mutation including classical and atypical forms has also been examined. DGJ effectively enhanced the enzyme activity in all three genotypes of cell strains derived from patients diagnosed as atypical Fabry disease, and some of the cell strains with classical Fabry forms having high residual enzyme activity. According to the present invention, a strategy of administrating an α-Gal A inhibitor should prove tobe an effective treatment for Fabry patients whose mutation occurs at the site other than catalytic center, and also should be useful for other glycosphingolipid storage diseases.

References cited herein are hereby incorporated by reference and are listed below for convenience:

1. R. O. Brady, A. E. Gal, R. M. Bradley, E. Martensson, A. L. Warshaw, and L. Laster, *N. Engl. J. Med.* 276, 1163 (1967).
2. R. J. Desnick, Y. A. Ioannou, and C. M. Eng, in *The Metabolic and Molecular Bases of Inherited Disease*, eds. C. R. Scriver, A. L. Beaudet, W. S. Sly, and D. Valle (McGraw-Hill, New York), pp. 2741 (1995).
3. S. Nakao, T. Takenaka, M. Maeda, C. Kodama, A. Tanaka, M. Tahara, A. Yoshida, M. Kuriyama, H. Hayashibe, H. Sakuraba, and H. Tanaka, *N. Engl. J Med.* 333, 288 (1995).
4. E. Beutler, *Science* 256, 794 (1992); F. M. Platt, G. R. Neises, G. Reikensmeier, M. J. Townsend, V. H. Perry, R. L Proia, B Winchester, R. A. Dwek, and T. D. Butters, *Science* 276, 428 (1997).

5. G. Romeo, M. D'Urso, A. Pisacane, E, Blum, A. de Falco, and A. Ruffilli, *Biochem. Genet* 13, 615 (1975); D. F. Bishop, G. A. Grabowski, and R. J. Desnick, *Am. J. Hum. Genet* 33, 71A (1981).
6. S. Ishii, R. Kase, H. Sakuraba, and Y. Suzuki, *Biochem. Biophys. Res. Comm.* 197, 1585 (1993).
7. S. Ishii, R. Kase, T. Okumiya, H. Sakuraba, and Y. Suzuki, *Biochem. Biophys. Res. Comm.* 220, 812 (1996).
8. A. Oshima, K. Yoshida, K. Itoh, R. Kase, H. Sakuraba, and Y Suzuki, *Hum Genet* 93, 109( 1994).
9. N. Asano, K. Oseki, H. Kizu, and K. Matsui, *J. Med. Chem.* 37, 3701 (1994); N. Asano, M. Nishiba, H. Kizu, K. Matsui, A. A. Watson, and R. J. Nash, *J. Nat. Prod.* 60, 98 (1997).
10. M. Shimmoto, R. Kase, K. Itoh, K. Utsumi, S. Ishii, C. Taya, H. Yonekawa, and H. Sakuraba, *FEBS Lett* 417, 89 (1997).
11. S. Ishii, R. Kase, H. Sakuraba, C. Taya, H. Yonekawa, T. Okumiya, Y. Matsuda, K. Mannen, M. Tekeshita, and Y. Suzuki, *Glycoconjugates J.* in press (1998).
12. T. Okumiya, S. Ishii, T. Takenaka, R. Kase, S. Kamei, H. Sakuraba, and Y. Suzuki, *Biochem. Biophys. Res. Comm.* 214, 1219 (1995)
13. S. Ishii, R. Kase, H. Sakuraba, S. Fujita, M. Sugimoto, K. Tomita, T. Semba, and Y. Suzuki, Biochim. *Biophys. Acta* 1204, 265 (1994).
14. S. Neuenhofer, G. Schwarzmann, H. Egge, and K. Sandhoff, *Biochemistry* 24, 525 (1985); S. Mitsutake, K. Kita, N. Okino, and M. Ito, Anal. Biochem. 247, 52 (1997).
15. G. Gilliland, S. Perrin, K. Blanchard, and H. F. Bunn, *Proc. Natl. Acad. Sci. USA* 87, 2725 (1990); TaKaRa Bio Catalog Vol. 1, D-59 (1997).
16. P. Lemansky, D. F. Bishop, R. J. Desnick, A. Hasilik, K. Von Figura, *J Biol. Chem.* 262, 2062 (1987).
17. S. M. Hurtley, and A. Helenius, Annual Rev. Cell Biol. 5, 277 (1989).
18. M. P. Dale, H. E. Ensley, K. Kern, K. A. R. Sastry and L. D. Byers, *Biochemistry* 24, 3530 (1985).
19. Folch et al. J. Biol. Chem. 226:497 (1957).
20. Fleisher, S. and M. Kervina, Methods in Enzymology 31, 6 (1974).

It will be appreciated that various modifications may be made in the invention as described above without departing from the scope and intent of the invention as defined in the following claims wherein:

What is claimed is:

1. A method of treating Fabry disease comprising administering to an individual in need thereof an effective amount of a compound of the formula:

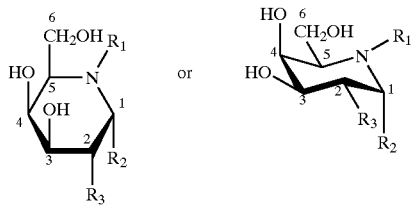

wherein $R_1$ represents H, $CH_3$, or $CH_2CH_3$; and $R_2$ and $R_3$ independently represent H, OH, a simple sugar, a 1-3 carbon alkyl, alkoxyl, or hydroxyalkyl group.

2. A method of treating Fabry disease comprising administering to an individual in need thereof an effective amount of a compound of the formula:

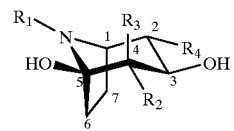

wherein for calystegine $A_3$: $R_1$=H, $R_2$=OH, $R_3$=H, $R_4$=H;

for calystegine $B_2$: R $R_1$=H, $R_2$=OH, $R_3$=H, $R_4$=H;

for calystegine $B_3$: $R_1$=H, $R_2$=H, $R_3$=OH, $R_4$=OH; and for N-methyl-calystegine: $R_1$=$CH_3$, $R_2$=OH, $R_3$=H, $R_4$=H.

3. A method of treating Fabry disease comprising administering to an individual in need thereof an effective amount of a compound of the formula:

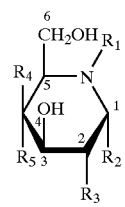

wherein $R_1$ represents H, $CH_3$, or $CH_2CH_3$;

$R_2$ and $R_3$ independently represent H, OH, a 1-6 carbon alkyl, hydroxyalkyl, alkoxy, or a simple sugar; and $R_4$ and $R_5$ independently represent H or OH.

4. A method of enhancing the activity of lysosomal α-galactosidase A in a mammalian comprising administering an effective amount of a compound of the formula:

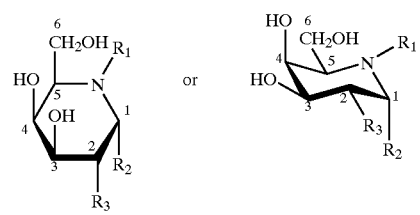

wherein $R_1$ represents H; $CH_3$, or $CH_2CH_3$; and $R_2$ and $R_3$ independently represent H, OH, a simple sugar, a 1-3 carbon alkyl, alkoxyl, or hydroxyalkyl group.

5. A method of enhancing the activity of lysosomal α-galactosidase A in a mammalian comprising administering an effective amount of a compound of the formula:

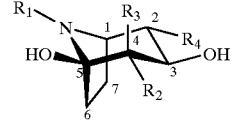

wherein for calystegine $A_3$: $R_1$=H, $R_2$=OH, $R_3$=H, $R_4$=H;

for calystegine $B_2$: $R_1$=H, $R_2$=OH, $R_3$=H, $R_4$=OH;

for calystegine $B_3$: $R_1$=H, $R_2$=H, $R_3$=OH, $R_4$=OH; and for N-methyl-calystegine: $R_1$=$CH_3$, $R_2$=OH, $R_3$=H, $R_4$=H.

6. A method of enhancing the activity of lysosomal α-galactosidase A in a mammalian comprising administering an effective amount of a compound of the formula:

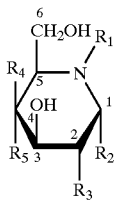

wherein $R_1$ represents H, $CH_3$, or $CH_2CH_3$;
$R_2$ and $R_3$ independently represent H, OH, a 1-6 carbon alkyl, hydroxyalkyl, alkoxy, or a simple sugar; and
$R_4$ and $R_5$ independently represent H or OH.

7. A method of stabilizing lysosomal α-galactosidase A in mammalian cells comprising administering an effective amount of a compound of formula:

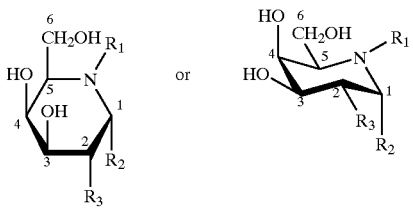

wherein $R_1$ represents H, $CH_3$, or $CH_2CH_3$; and
$R_1$ and $R_3$ independently represent H, OH, a simple sugar, a 1-3 carbon alkyl, alkoxyl, or hydroxyalkyl group.

8. A method of stabilizing lysosomal α-galactosidase A in mammalian cells comprising administering an effective amount of a compound of formula:

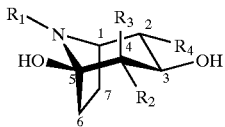

wherein for calystegine $A_3$: $R_1$=H, $R_2$=OH, $R_3$=H, $R_4$=H;
for calystegine $B_2$: $R_1$=H, $R_2$=OH, $R_3$=H, $R_4$=OH;
for calystegine $B_3$; $R_1$=H, $R_2$=H, $R_3$=OH, $R_4$=OH; and
for N-methyl-calystegine: $R_1$=$CH_3$, $R_2$=OH, $R_3$=H, $R_4$=H.

9. A method of stabilizing lysosomal α-galactosidase A in mammalian cells comprising administering an effective amount of a compound of formula:

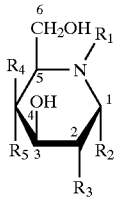

wherein $R_1$ represents H, $CH_3$, or $CH_2CH_3$;
$R_2$ and $R_3$ independently represent H, OH, a 1-6 carbon alkyl, hydroxyalkyl, alkoxy, or a simple sugar; and
$R_4$ and $R_5$ independently represent H or OH.

10. A method of preventing the degradation of lysosomal α-galactosidase A in a mammalian comprising administering an effective amount of a compound of the formula:

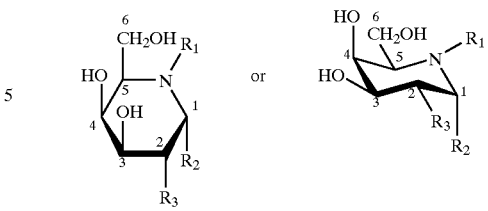

wherein $R_1$ represents H, $CH_3$, or $CH_2CH_3$; and
$R_2$ and $R_3$ independently represent H, OH, a simple sugar, a 1-3 carbon alkyl, alkoxyl, or hydroxyalkyl group.

11. A method of preventing the degradation of lysosomal α-galactosidase A in a mammalian comprising administering an effective amount of a compound of the formula:

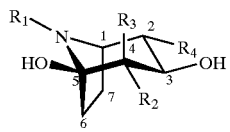

wherein for calystegine $A_3$: $R_1$=H, $R_2$=OH, $R_3$=H, $R_4$=H;
for calystegine $B_2$: $R_1$=H, $R_2$=OH, $R_3$=H, $R_4$=OH;
for calystegine $B_3$; $R_1$=H, $R_2$=H, $R_3$=OH, $R_4$=OH; and
for N-methyl-calystegine: $R_1$=$CH_3$, $R_2$=OH, $R_3$=H, $R_4$=H.

12. A method of preventing the degradation of lysosomal α-galactosidase A in a mammalian comprising administering an effective amount of a compound of the formula:

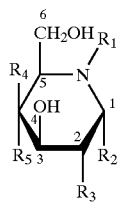

wherein $R_1$ represents H, $CH_3$, or $CH_2CH_3$;
$R_2$ and $R_3$ independently represent H, OH, a 1-6 carbon alkyl, hydroxyalkyl, alkoxy, or a simple sugar; and
$R_4$ and $R_5$ independently represent H or OH.

13. A method of preventing deposition of neutral glycosphingolipids in vascular endothelial cells in an individual in need thereof, comprising administering an effective amount of a compound of formula:

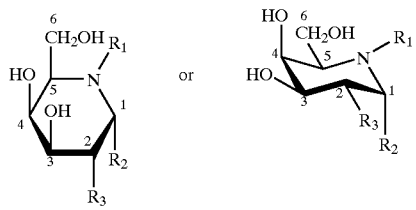

wherein $R_1$ represents H, $CH_3$, or $CH_2CH_3$; and
$R_2$ and $R_3$ independently represent H, OH, a simple sugar, a 1-3 carbon alkyl, alkoxyl, or hydroxyalkyl group.

14. A method of preventing deposition of neutral glycosphingolipids in vascular endothelial cells in an individual in need thereof, comprising administering an effective amount of a calystegine compound of formula:

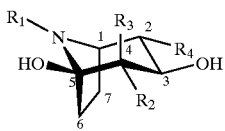

wherein for calystegine $A_3$: $R_1$=H, $R_2$=OH, $R_3$=H, $R_4$=H;
for calystegine $B_2$: $R_1$=H, $R_2$=OH, $R_3$=H, $R_4$=OH;
for calystegine $B_3$: $R_1$=H, $R_2$=H, $R_3$=OH, $R_4$=OH; and
for N-methyl-calystegine: $R_1$=$CH_3$, $R_2$=OH, $R_3$=H, $R_4$=H.

15. A method of preventing deposition of neutral glycosphingolipids in vascular endothelial cells in an individual in need thereof, comprising administering an effective amount of a compound of formula:

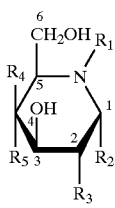

wherein $R_1$ represents H, $CH_3$, or $CH_2CH_3$;
$R_2$ and $R_3$ independently represent H, OH, a 1-6 carbon alkyl, hydroxyalkyl, alkoxy, or a simple sugar; and
$R_4$ and $R_5$ independently represent H or OH.

16. The method of claim 15, wherein the compound is selected from the group consisting of 1-deoxynojirimycin, 1-deoxygalactonojirimycin, α-homonojirimycin, 3,4-diepi-α-homonojirimycin, and 4-epi-fagomine.

17. The method of claim 16 wherein the compound is 1-deoxygalactonojirimycin.

18. The method of claim 13, wherein the glycosphingolipids are predominantly ceramide trihexoside.

19. The method of claim 14, wherein the glycosphingolipids are predominantly ceramide trihexoside.

20. The method of claim 15, wherein the glycosphingolipids are predominantly ceramide trihexoside.

21. A method of preventing renal failure associated with deposition of neutral glycosphingolipids in vascular endothelial cells in an individual in need thereof, comprising administering an effective amount of a compound comprising administering an effective amount of a compound of formula:

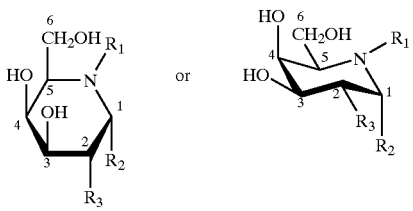

wherein $R_1$ represents H, $CH_3$, or $CH_2CH_3$; and
$R_2$ and $R_3$ independently represent H, OH, a simple sugar, a 1-3 carbon alkyl, alkoxyl, or hydroxy-alkyl group.

22. A method of preventing renal failure associated with deposition of neutral glycosphingolipids in vascular endothelial cells in an individual in need thereof, comprising administering an effective amount of a calystegine compound comprising administering an effective amount of a compound of formula:

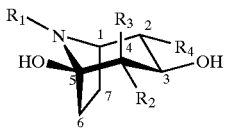

wherein for calystegine $A_3$: $R_1$=H, $R_2$=OH, $R_3$=H, $R_4$=H;
for calystegine $B_2$: $R_1$=H, $R_2$=OH, $R_3$=H, $R_4$=OH;
for calystegine $B_3$: $R_1$=H, $R_2$=H, $R_3$=OH, $R_4$=OH; and
for N-methyl-calystegine: $R_1$=$CH_3$, $R_2$=OH, $R_3$=H, $R_4$=H.

23. A method of preventing renal failure associated with deposition of neutral glycosphingolipids in vascular endothelial cells in an individual in need thereof, comprising administering an effective amount of a compound comprising administering an effective amount of a compound of formula:

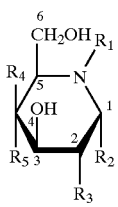

wherein $R_1$ represents H, $CH_3$, or $CH_2CH_3$;
$R_2$ and $R_3$ independently represent H, OH, a 1-6 carbon alkyl, hydroxyalkyl, alkoxy, or a simple sugar; and
$R_4$ and $R_5$ independently represent H or OH.

24. The method of claim 23, wherein the compound is selected from the group consisting of 1-deoxynojirimycin, 1-deoxygalactonojirimycin, α-homonojirimycin, , 3,4-diepi-α-homonojirimycin, and 4-epi-fagomine.

25. The method of claim 24 wherein the compound is 1-deoxygalactonojirimycin.

26. The method of claim 21, wherein the glycosphingolipids are predominantly ceramide trihexoside.

27. The method of claim 22, wherein the glycosphingolipids are predominantly ceramide trihexoside.

28. The method of claim 23, wherein the glycosphingolipids are predominantly ceramide trihexoside.

29. A method of preventing premature myocardial infarctions and strokes associated with deposition of neutral glycosphingolipids in vascular endothelial cells in an individual in need thereof, comprising administering an effective amount of a compound of formula:

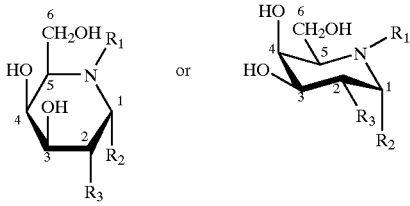

wherein $R_1$ represents H, $CH_3$, or $CH_2CH_3$; and $R_2$ and $R_3$ independently represent H, OH, a simple sugar, a 1-3 carbon alkyl, alkoxyl, or hydroxy-alkyl group.

30. A method of preventing premature myocardial infarctions and strokes associated with deposition of neutral glycosphingolipids in vascular endothelial cells in an individual in need thereof, comprising administering an effective amount of a compound of formula:

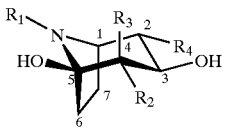

wherein for calystegine $A_3$: $R_1$=H, $R_2$=OH, $R_3$=H, $R_4$=H;

for calystegine $B_2$: $R_1$=H, $R_2$=OH, $R_3$=H, $R_4$=OH;

for calystegine $B_3$; $R_1$=H, $R_2$=H, $R_3$=OH, $R_4$=OH; and for N-methyl-calystegine: $R_1$=$CH_3$, $R_2$=OH, $R_3$=H, $R_4$=H.

31. A method of preventing premature myocardial infarctions and strokes associated with deposition of neutral glycosphingolipids in vascular endothelial cells in an individual in need thereof, comprising administering an effective amount of a compound of formula:

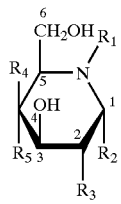

wherein $R_1$ represents H, $CH_3$, or $CH_2CH_3$;

$R_2$ and $R_3$ independently represent H, OH, a 1-6 carbon alkyl, hydroxyalkyl, alkoxy, or a simple sugar; and $R_4$ and $R_5$ independently represent H or OH.

32. The method of claim 31, wherein the compound is selected from the group consisting of 1-deoxynojirimycin, 1-deoxygalactonojirimycin, α-homonojirimycin, 3,4-diepi-α-homonojirimycin, and 4-epi-fagomine.

33. The method of claim 32 wherein the compound is 1-deoxygalactonojirimycin.

34. The method of claim 29, wherein the individual has the a typical variant form of Fabry disease.

35. The method of claim 30, wherein the individual has the a typical variant form of Fabry disease.

36. The method of claim 31, wherein the individual has the a typical variant form of Fabry disease.

37. The method of claim 29, wherein the glycosphingolipids are predominantly ceramide trihexoside.

38. The method of claim 30, wherein the glycosphingolipids are predominantly ceramide trihexoside.

39. The method of claim 31, wherein the glycosphingolipids are predominantly ceramide trihexoside.

* * * * *

UNITED STATES PATENT AND TRADEMARK OFFICE
CERTIFICATE OF CORRECTION

PATENT NO. : 6,774,135 B2
DATED : August 10, 2004
INVENTOR(S) : Jian-Qiang Fan and Satoshi Ishii It is certified that error appears in the above-identified patent and that said Letters Patent is hereby corrected as shown below:

Column 12,
Lines 33, 50 and 66, insert the word -- cell -- in front of the word "mammalian."
Line 46, replace the first semicolon with a comma to read -- wherein $R_1$ represents H, $CH_3$, or $CH_2CH_3$; and --.

Column 13,
Line 66, insert the word -- cell -- in front of the word "mammalian."

Column 14,
Lines 16 and 31, insert the word -- cell -- in front of the word "mammalian."

Column 15,
Lines 48-49, delete the first instance of the following "comprising administering an effective amount of a compound"

Column 16,
Lines 3-4, delete the phrase "administering an effective amount of a calystegine compound"
Lines 21-22, delete the first instance of the following "comprising administering an effective amount of a compound"

Column 18,
Lines 21, 23 and 25, replace "a typical" with -- atypical --.

Signed and Sealed this

Twenty-ninth Day of March, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,774,135 B2 | Page 1 of 2 |
| APPLICATION NO. | : 09/927285 | |
| DATED | : August 10, 2004 | |
| INVENTOR(S) | : Jian-Qiang Fan et al. | |

It is certified that error appears in the above-identified patent and that said Letters Patent is hereby corrected as shown below:

Col. 12 Claim 2, line 6: replace the phrase -- for calystegine $B_2$: R $R_1$=H, $R_2$=OH, $R_3$=H, $R_4$=H -- with the phrase -- for calystegine $B_2$: $R_1$=H, $R_2$=OH, $R_3$=H, $R_4$=OH --

Col. 12 Claim 2, line 8: replace the phrase -- for N-methyl calystegine: $R_1$=$CH_3$, $R_2$=OH, $R_3$=H, $R_4$=H -- with the phrase -- for N-methyl calystegine $A_3$: $R_1$= $CH_3$, $R_2$=OH, $R_3$=H, $R_4$=H --

Col. 12 Claim 5, lines 8-9: replace the phrase -- for N-methyl calystegine: $R_1$=$CH_3$, $R_2$=OH, $R_3$=H, $R_4$=H -- with the phrase -- for N-methyl calystegine $A_3$: $R_1$= $CH_3$, $R_2$=OH, $R_3$=H, $R_4$=H --

Col. 13 Claim 8, lines 8-9: replace the phrase -- for N-methyl calystegine: $R_1$=$CH_3$, $R_2$=OH, $R_3$=H, $R_4$=H -- with the phrase -- for N-methyl calystegine $A_3$: $R_1$= $CH_3$, $R_2$=OH, $R_3$=H, $R_4$=H --

Col. 14 Claim 11, lines 8-9: replace the phrase -- for N-methyl calystegine: $R_1$=$CH_3$, $R_2$=OH, $R_3$=H, $R_4$=H -- with the phrase -- for N-methyl calystegine $A_3$: $R_1$= $CH_3$, $R_2$=OH, $R_3$=H, $R_4$=H --

Col. 15 Claim 14, lines 8-9: replace the phrase -- for N-methyl calystegine: $R_1$=$CH_3$, $R_2$=OH, $R_3$=H, $R_4$=H -- with the phrase -- for N-methyl calystegine $A_3$: $R_1$= $CH_3$, $R_2$=OH, $R_3$=H, $R_4$=H --

Col. 15 Claim 22, lines 8-9: replace the phrase -- for N-methyl calystegine: $R_1$=$CH_3$, $R_2$=OH, $R_3$=H, $R_4$=H -- with the phrase -- for N-methyl calystegine $A_3$: $R_1$= $CH_3$, $R_2$=OH, $R_3$=H, $R_4$=H --

UNITED STATES PATENT AND TRADEMARK OFFICE
CERTIFICATE OF CORRECTION

PATENT NO. : 6,774,135 B2
APPLICATION NO. : 09/927285
DATED : August 10, 2004
INVENTOR(S) : Jian-Qiang Fan et al.

It is certified that error appears in the above-identified patent and that said Letters Patent is hereby corrected as shown below:

Col. 16 Claim 30, lines 8-9: replace the phrase -- for N-methyl calystegine: $R_1=CH_3$, $R_2=OH$, $R_3=H$, $R_4=H$ -- with the phrase -- for N-methyl calystegine $A_3$: $R_1=CH_3$, $R_2=OH$, $R_3=H$, $R_4=H$ --

Signed and Sealed this

Twenty-sixth Day of May, 2009

JOHN DOLL
*Acting Director of the United States Patent and Trademark Office*